Figure 1:
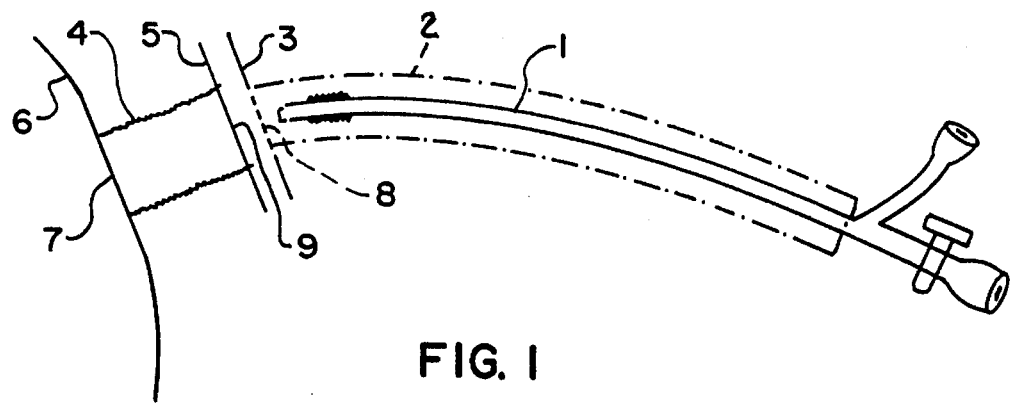

United States Patent [19]
Daneshvar

[11] Patent Number: 5,582,599
[45] Date of Patent: Dec. 10, 1996

[54] CLEAN CATHETER INSERTION SYSTEM

[76] Inventor: Yousef Daneshvar, 21459 Woodfarm, Northville, Mich. 48167

[21] Appl. No.: 279,403

[22] Filed: Jul. 25, 1994

[51] Int. Cl.⁶ ........................................ A61M 5/00
[52] U.S. Cl. .................. 604/263; 604/172; 604/171; 206/364; 206/438
[58] Field of Search ........................ 604/163, 171, 604/172, 263, 283, 264; 206/363–365, 306, 361–362, 438

[56] References Cited

U.S. PATENT DOCUMENTS

| | | | |
|---|---|---|---|
| 3,361,253 | 1/1968 | Lonholdt | 206/363 |
| 3,648,704 | 3/1972 | Jackson | 604/172 |
| 3,861,395 | 1/1975 | Taniguchi | 206/364 |
| 3,898,993 | 8/1975 | Taniguchi | 604/172 |
| 3,967,728 | 7/1976 | Gordon | 206/364 |
| 4,140,127 | 2/1979 | Cianci | 206/364 |
| 4,226,328 | 10/1980 | Beddow | 206/364 |
| 4,269,310 | 5/1981 | Uson | 604/172 |
| 4,419,097 | 12/1983 | Rowland | 604/174 |
| 4,522,302 | 6/1985 | Paikoff | 206/364 |
| 4,710,169 | 12/1987 | Christopher | 604/171 |
| 4,754,877 | 7/1988 | Johansson | 206/364 |
| 4,772,275 | 9/1988 | Erlich | 206/364 |
| 4,810,247 | 3/1989 | Glassman | 604/174 |
| 4,811,847 | 3/1989 | Reif | 206/364 |
| 4,954,239 | 9/1990 | Mueller | 206/364 |
| 5,100,396 | 3/1992 | Zamierowski | 604/174 |
| 5,116,319 | 5/1992 | van den Haak | 604/197 |
| 5,226,530 | 7/1993 | Golden | 206/364 |
| 5,236,422 | 8/1993 | Eplett | 604/174 |
| 5,242,398 | 9/1993 | Knoll | 604/171 |
| 5,346,478 | 9/1994 | Jinotti | 604/163 |
| 5,429,234 | 7/1995 | Bohannon | 206/362 |

*Primary Examiner*—Randall L. Green
*Assistant Examiner*—Chalin Smith

[57] ABSTRACT

This invention introduces a new means and units that are to allow a rapid and clean insertion of bladder and similar catheters. These units will isolate and cover the contaminated surrounding areas by a cover made from synthetic or natural materials and their combinations. It also introduces a series of catheter covers that will cover the bladder catheters and will prevent it from being contaminated. These units also may use means that allows the support of the catheter to be done easily. Thank you very much for your consideration.

20 Claims, 7 Drawing Sheets

1

CLEAN CATHETER INSERTION SYSTEM

THE BACKGROUND OF THE INVENTION

The problem with urination and the need for the insertion of bladder catheters is well known; this problem may occur anywhere. Many times the place isn't ideal, clean, or comfortable enough for such a procedure. Therefore the sanitation and sterilization of the field which is essential for proper medical care is not possible all the time and therefore there is a higher chance of infection when the bladder catheter touches contaminated areas during or after the insertion into the bladder. These units are intended to prevent such a problem.

THE BRIEF EXPLANATION OF INVENTION

This invention deals with models of bladder catheters that will be protected and placed by clear covers that will allow the utilization of such units to be done without the hands of the user touching the catheters; therefore they will decrease the chances of contamination. Furthermore, the invention also introduces systems that will allow the catheters to be kept inside the covers for the prevention of future contamination and also will allow catheters to be held by a support system.

THE BRIEF EXPLANATIONS OF THE FIGURES

FIG. 1. Shows a bladder catheter 1 with a protective cover 2

Figure 2:
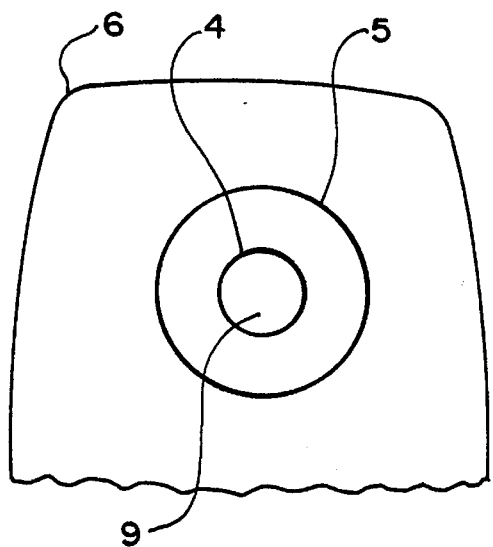

FIG. 2. Shows the front view of the cover for cleaning.

Figure 3:
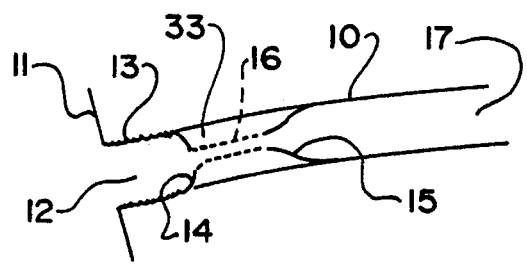

FIG. 3. Shows a cover that can be placed easily at the tip of the penis

Figure 4:
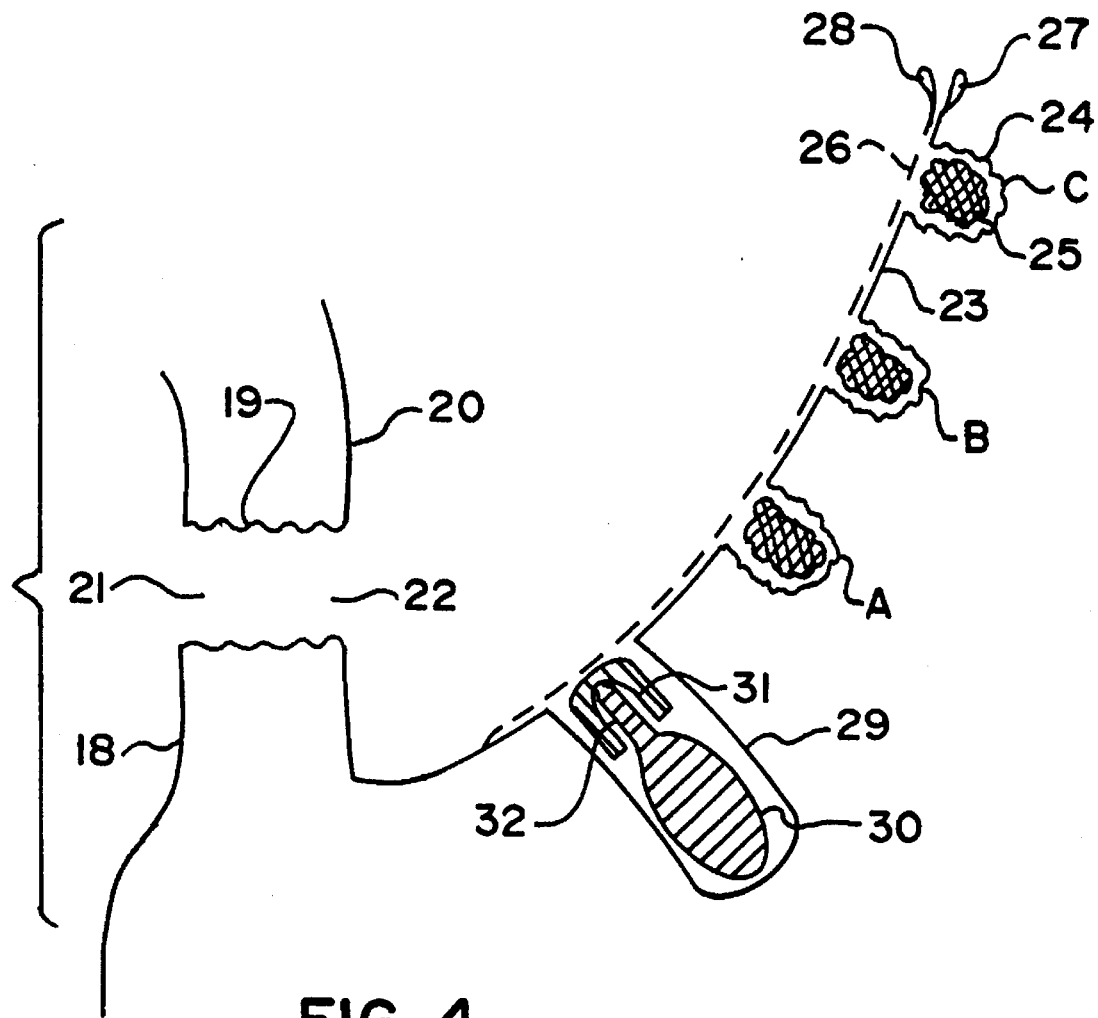

FIG. 4. Shows a cover for the easy cleaning and anesthetic application of the external urethra.

Figure 5:
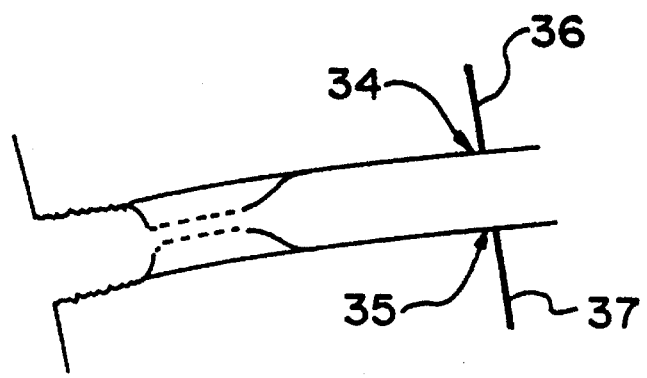

FIG. 5. Shows the end piece of a model of a bladder catheter cover that can separated along the line marked at arrows 34–35.

Figure 6:
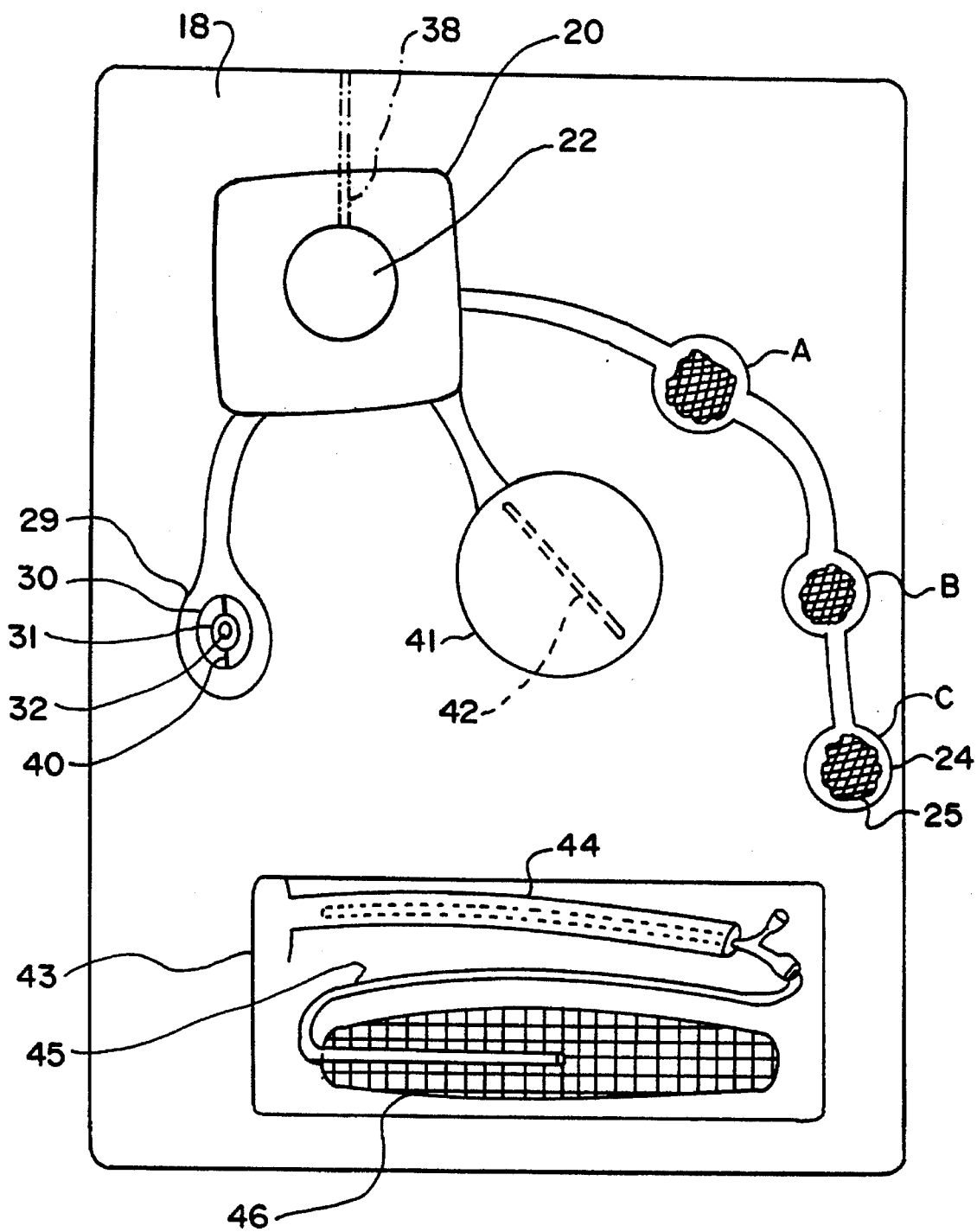

FIG. 6. Shows a model of a complete unit that allows an easy and rapid insertion of the bladder catheter FIG. 7. Shows a bladder catheter with a piece 49 for a better grip of the catheter as well as a specially-shaped wall shown at 50 & 51

Figure 8:
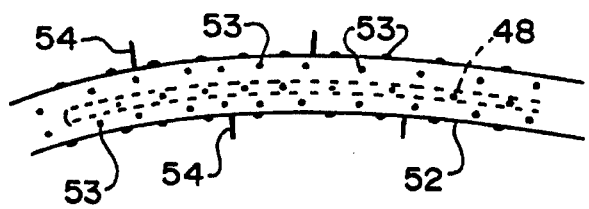

FIG. 8. Shows a catheter cover which has extra spots or bump on the outer surface of its wall.

Figure 9:
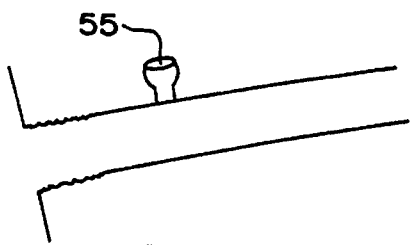

FIG. 9. Shows the end piece of a catheter cover that has an opening for injection of a gel FIG. 10. Shows a unit similar to FIG. 9 with a tube of gel or medicated material connected to it.

Figure 11:
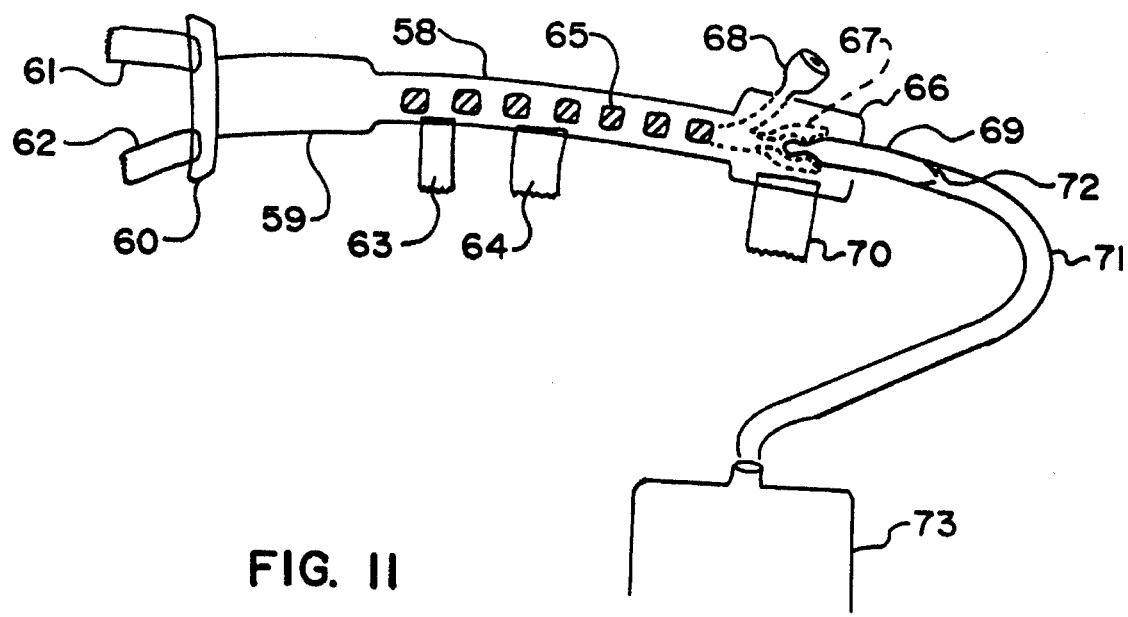

FIG. 11. Show some of the important features of some models of these units.

Figure 12:
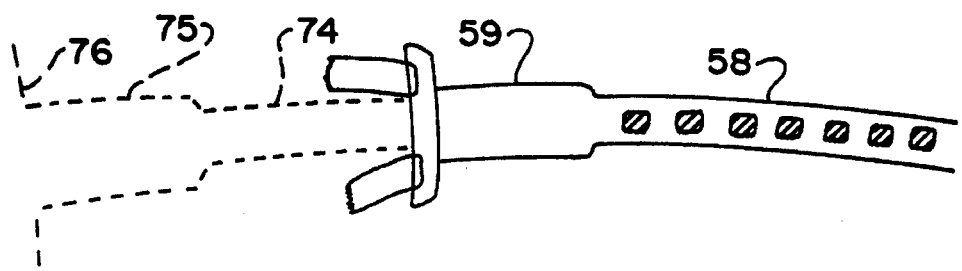

FIG. 12. Shows a cover with two pieces

Figure 13:
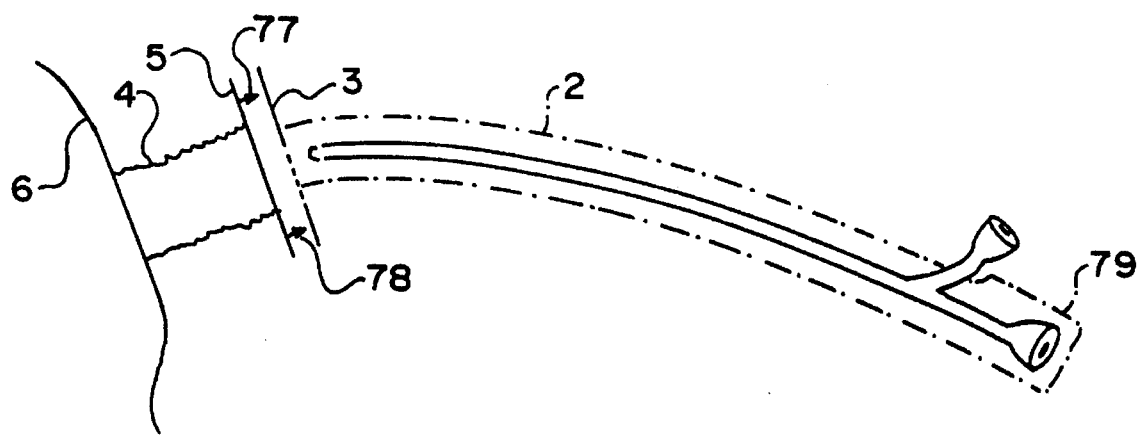

FIG. 13. Shows a unit similar to the FIG. 1 with snaps shown at 77 & 78

Figure 14:
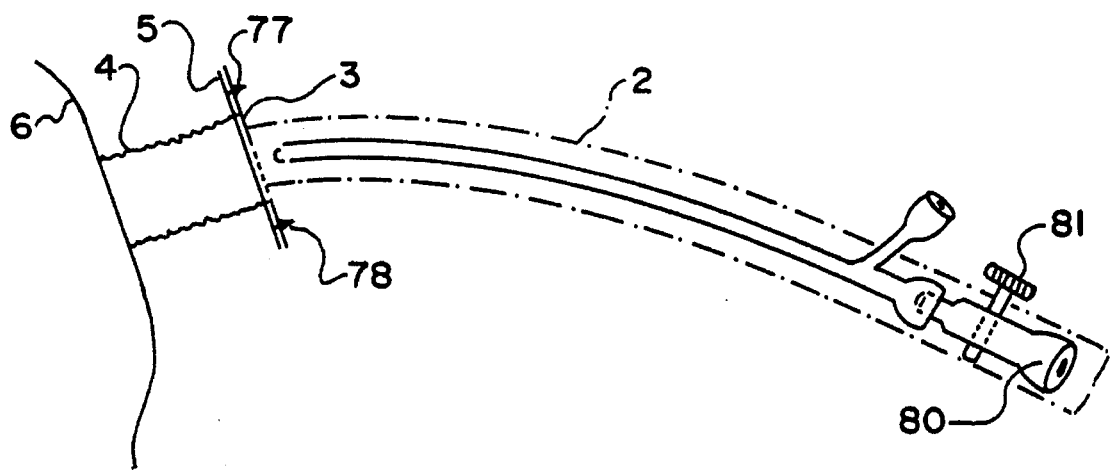

FIG. 14. Shows the pieces 3 & 5 connected to each other by snaps.

Figure 15:
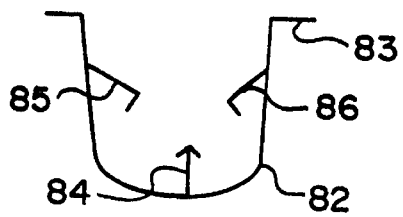

FIG. 15. Shows the cross cut of the space for holding the cotton balls for disinfections.

Figure 16:
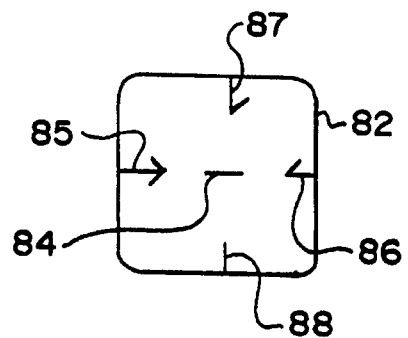

FIG. 16. Shows the cross cut view of the unit shown at previous FIG. 15.

Figure 17:
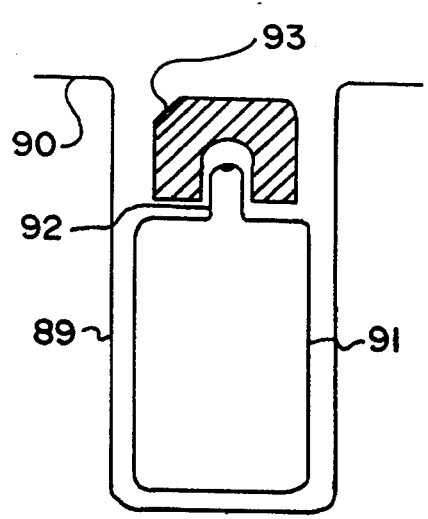

FIG. 17. Shows another view of the space that will hold the medication for anesthesia.

Figure 18:
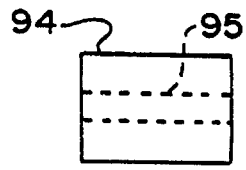

FIG. 18. Shows a small, soft balloon to be placed around the catheter.

Figure 19:
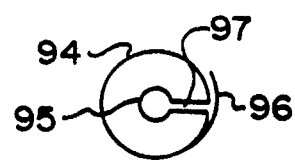

FIG. 19. Shows the cross cut view of the unit shown in previous FIG. 18.

THE DETAILED EXPLANATIONS OF THE FIGURES

FIG. 1. This figure schematically shows a bladder catheter 1 that has a protective cover 2 on it which will prevent the contamination of this catheter by hand contact from occurring at the time of use. This cover will be made from a polymer or combination of a synthetic such as vinyl and natural materials such cotton or paper and any similar materials. It may also be made from elastic material or may have elastic components as well in order to get shorter after the insertion of the catheter inside the bladder since the length of the catheter outside the urethra will be shorter. It may be shaped to be flat or like the wall of accordion. The end piece of this cover may have any proper shape but importantly may have a flat piece or fan out to have the piece 3 that will fit and stand around the penis and allow it to be held in place securely. This piece 3 will have an opening 8 that will allow the penis or the opening of the external urethra of the female to fit inside it for easily handling. The bladder catheter is shown at 1 and importantly can be made in any kind and shape that will be desired. This figure also shows the middle body of a cleaning cover marked at 4 that will be placed around the penis of the patient so that it will allow the penis to be held securely inside this piece in order to be cleaned. This piece, referred to as the cleaning piece, will also have the apron 6 that may have different sizes but basically will be a large cover to be placed around the base of the penis or the external opening of the urethra. This piece will have an opening 7 that will allow the penis to enter inside its tubing 4. This tubing 4 may have a flat wall, may be elastic or can have a wall in the shape of the wall of accordion so that its length can be adjusted according to the length of the penis. The other end of this unit 9 will have a cover 5 to stand and cover the hand of the user and will prevent the hand of the user from being contaminated. At the time of use the penis of the patient will be placed into the tubing 4 of this unit through the opening 7 to come out at opening 9. The tube 4 will stand around the penis and the hand of the user will be around the outer surface of the tube 4. The size of the apron 6 will vary and commonly it will be large to cover the area and prevent the contamination of the whole area. The piece 4 and it related parts may have a connection line or a line that will allow this piece to be torn or separated along it in order to be removed after use.

FIG. 2. This figure schematically shows the front view of the cover for cleaning. This will be the unit that will be placed around the tip of the penis or the external opening of the urethra. When placed on a man, the tip of the penis of the patient will be inside the opening 9. The wall of the tubing that will hold the penis inside is shown at 4 and the small cover that will stand around the penis and over the hand of the user is at 5. Only the upper part of the larger apron or cover 6 is shown in this figure.

FIG. 3. This figure schematically shows a model of the cover for the bladder catheter that has a special design that will allow it to be easily placed at the tip of the penis due to its concave curve 14. It also has a small space 33 which has a perforated wall marked at 16 which will hold a lubricant or medicated gel such as anesthetic gel in order to be placed over the bladder catheter during its passage through this part. The benefit of this piece will be to eliminate the need for using a gel and its application to the surface of the catheter. This method will allow the benefit of different medications such as anesthetic, antibiotics and different medications to be used. Importantly the wall 15 of this part has a funnel shape in order to allow the bladder catheter to be directed and fed into this piece easily. In this figure the body of the cover is shown at 10 and the piece that fans out or expands to stand around the base of the penis at 11. The opening 12 is for the penis to fit in and this unit will have a slightly expanded part marked at 13 that is to accept the penis inside comfortably. The wall of this part may be shaped from an accordion wall type of material to expand if needed. The bladder catheter will be placed inside the opening 17. Please notice that this figure only shows the front part of such a cover.

FIG. 4. This figure schematically shows a model of the cover unit that is to allow easy and less time consuming cleaning and anesthetic application of the external urethra. In this figure a cover which has a large apron 18 has a tubing 19 that will stand around the penis. Due to its accordion type wall, its length can be adjusted to the length of the penis. This unit has the opening 21 which is for the penis to be inserted in and an opening 22 for the tip of the penis to be placed for cleaning purpose. The cover 20 and its continuation 23 will stand around the penis to prevent the hand of the user from being contaminated with cleaning material. This unit is enriched with a few further units. One of them is a series of spaces marked at A, B & C that are like pockets made from polymer, and each one of these spaces (such as the one shown at 24) will hold a piece of disinfectant such as a cotton ball 25 which is saturated with a disinfectant such as Iodine so it can be used for cleaning the area. Importantly, these sponges or cotton balls may be connected to their surrounding cover, its inner wall or its base by a thread, a small screen or a similar means so that this connection would prevent the cotton ball or sponge from falling out of the cover after use. This will allow them to be under control. Their space may also have a small cover piece to cover them after use to prevent contaminating the rest of the area. These pieces will have a protective cover 26 which is to be removed prior to the use of this unit. The tabs 27 and 28 are designed to allow an easy and quick separation of these covers. This figure also shows a pocket 29 that is to hold a small container that is to keep a dose of anesthetic gel inside it. This container can be made in the shape of a tubing such as tooth paste or in shape of a bulb 30 made from rubber or a similar polymer with a properly-sized end tip 32 that is soft and shaped to easily fit the orifice of the external urethra so that at the time of the use the tip 32 of this unit will be inserted into the external urethra and will allow injection of the anesthetic medication inside the urethra to occur in order to prevent pain and irritation. The tip of this unit 32 is to have a cover 31 with a large handle to allow it to be opened easily.

This cover unit may also have a small envelope or bag (not shown here) in order to allow the used materials of these units to be placed inside it for disposal purposes. This disposal pocket may have a flap or rim to keep the used materials inside.

This cover unit also may have a perforated line to allow this unit to be torn off and removed easily after use. These cover units are also to have a series of lines, markings and figures that will allow special directions or instructions to be shown or communicated to the users.

FIG. 5. This figure shows only the end piece of a model of a bladder catheter cover that has two pieces separated along the line marked at arrows 34–35. This will allow the separation of the end piece of this unit from the body of the unit to occur so that after use, the rest of the cover can be kept over the bladder catheter in order to allow protection to be continued and to prevent the contamination of the catheter even after the placement process is over. In this figure a wall marked at 36 and 37 will have a series of holes or means to be connected to a band or strap to allow it to be held in place securely. This band or strap will go around the belt area to hold this unit in place securely. Alternatively, this piece may be connected to a support unit that is designed to hold such a catheter in place securely and is part of this inventor's U.S. Pat. No. 5,460,606.

FIG. 6. This figure schematically shows a model of such a protective cover which is part of the whole complete unit that allows an easy and rapid insertion of the bladder catheter to occur in a sterile fashion without a need for any other piece. In this unit a basic cover 18 made from a layer of plastic or paper or their combination will be used. This unit is to be impermeable for fluid and germs and other contaminating materials. This layer will have the make up of protecting the area under it from contamination. This cover is shown at 18. It will be large enough to cover the whole need area. This cover will also have an opening 22 in its upper center area that will allow the tip of the penis or the opening of the urethra in the females to be placed. In the case of men, the tip of the penis will be inside the opening 22 and the smaller cover 20 will stand around the penis and over the hand of the user so it will prevent the hand of the user from being contaminated with the cleaning material. The unit shown in this picture will have all the needed pieces that are required for the procedure of the bladder catheter: it has the series of the pockets A, B & C which hold the pieces of the disinfectants. Importantly these are conveniently designed and made so that the user does not need to take them out of their covering pocket for use and simply can hold the outer wall of the pocket 24 between his/her two fingers to rub the cotton ball 25 against the orifice of the external urethra to clean it. This is believed to facilitate this job significantly and may also be used in many other similar conditions. The number of these medicated cotton balls or sponges will vary to satisfy the rule of such a procedure. The used cotton balls or sponges will be left inside their own cover and then the others will be used. A small cover piece may be used to cover the used cotton balls and prevent the contamination of the other areas from occurring. As mentioned earlier, a small band or a similar means will be used to keep these cleaning pieces inside their covers during use. A tighter opening of their pockets may also serve this purpose as well. In this figure a bag 41 is to be used for disposal purposes and it has an opening marked at 42 that will allow the placement of the waste inside it. The anesthetic medication or the lubricant gel will be kept inside the space or the pocket 29. The anesthetic medication will be kept inside a small container 30 which may have different shapes and make ups. As mentioned earlier in FIG. 4 this container may have any proper shape such as a tooth paste tube or like a bulb made from rubber or a similar polymer with a proper size. The end tip 32 of this unit will be soft and shaped to fit easily in the orifice of the external urethra of the patient so that at the time of use, the tip 32 of this unit will be inserted into the external urethra of the patient to allow injection of the anesthetic medication inside the urethra to be done easily. The tip of this container will have the cover 31 which has a large handle 40 that is to allow it to be opened easily. The line 38 and its continuation in the big cover are to show symbolically how this unit will have a line to allow it to be easily separated and removed after the procedure is over. This large unit also has the pocket 43 which is to symbolically show how such a pocket will be present in order to hold all the needed pieces for this procedure. For example the bladder catheter cover shown at 44, the bladder catheter inside it, the related tubing 45 and the bag 46 all will be packed and ready to be used. Other needed units such as a pair of gloves (which may not be actually needed), a small container to receive sample of the urine if it was wanted and similar things will also be included although they are not shown here. Importantly these units also will have a unit like a bulb or a syringe containing water in order to allow a rapid infusion of water inside the balloon of the catheter. The person will be able to squeeze the bulb or the syringe of water or air into the balloon in order to secure the placement of the catheter; this is not shown in this figure as well. Overall, it will be a complete and advanced unit to allow this important job to be done easier, faster and in a sterile condition. The base of this cover will function as a disposal cover so that after use, all the used materials and the waste will be wrapped inside it to be disposed conveniently. This unit may have a band of adhesive with a cover to allow it to be stuck to the area of use in order to prevent it from slipping and falling. Also it may have adhesive bands to allow it to be kept close for disposal purpose. This larger cover 18 will also have a line to allow this unit to be torn off and removed easily after use. These units are also to have a series of lines, markings and figures that will allow special directions or instructions to be communicated to the users.

Figure 7:
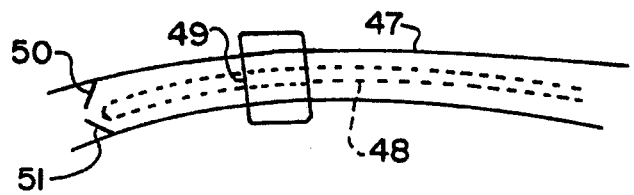

FIG. 7. This figure shows the tip of a bladder catheter 48 that has a protective cover 47 on it; however, this protective cover also has a special piece 49 that will stand on it to allow it to be squeezed against the wall of the cover and the catheter in order to allow an easier grip to occur. There may be more than one of these and they may be moved from one spot to another. Importantly, this unit also shows how a specially-shaped wall such as the one shown at 50 & 51 may be placed in order to allow the bladder catheter to be pushed forward easily but to prevent it from sliding back again during the insertion period. This wall may be placed in any proper area and can be multiple.

FIG. 8. This figure is to show how the wall of the catheter cover may be made to have extra spots or bumps made in the wall of this unit in order to allow a better grip of this unit and the catheter to occur. In this figure the outer surface of this cover 52 has numbers of the bumps marked at 53 that will allow a better grip for the user and they are to prevent the cover from slipping away; also this cover may have a series of tabs shown at 54 that will allow the cover to be held and repositioned as desired. Importantly instead of these bumps the cover may have a series of raised lines in different shapes, configurations or directions to allow the same purpose for a better grip to occur. Also importantly the inner surface of these covers may also have such a series of bumps or lines to provide a better grip as well.

FIG. 9. This figure shows only the end piece of a model of a protective bladder catheter cover that has an opening 55 that allows the injection of a gel or a medicated material such as an anesthetic gel inside this cover to occur. This will facilitate the work and will eliminate the job of a person to apply the gel over the catheter manually. The chances of contamination will decrease as well.

Figure 10:
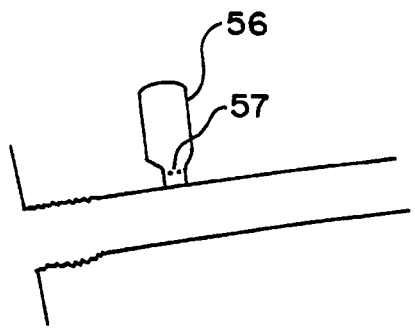

FIG. 10. This figure shows a unit similar to the one shown in the previous FIG. 9. Except in this model the cover has a tube of gel or medicated material shown at 56 in place and connected to it. This unit has a wall of 57 that at the time of use will be broken or torn off by tilting, twisting or a similar simple action and mechanism so that it will allow the injection of the gel or a medicated material inside the cover to occur easily. This will facilitate the work of such a job even further and will eliminate the job of a person applying the gel over the catheter manually.

FIG. 11. This figure is to show some of the important features of some models of these units. In this figure the cover unit shown at 58 has a series of patches made from a semi-hard or hard polymer which has a concave outer curve (and a flat or curved inner surface) to allow the tip of the fingers to fit on it easily and comfortably and these are to allow the unit to be squeezed by holding the two of these patches simultaneously. This design is to make the movement of the catheter easier and faster. This unit also has a tubular shaped area 59 that will be sized to fit the penis comfortably and to hold it inside. The material that will make this part may be a non-irritant material. The end of this piece 59 marked at 60 is a piece that will fit the outer area of the body next to the base of the penis so that it will stand on it comfortably. Then the straps shown at 61, 62 and their counterparts from the other side can be tied on the belt area as well as the thigh in order to hold this unit in place securely. The body of this unit also has other bands 63, 64 and their counterparts from the other side that will be taped or wrapped around the thigh in order to allow the unit to be held in place securely. Importantly this unit may have a piece at its end such as one shown at 66 that will function as a cradle to hold the end of the catheter inside itself safely to prevent the catheter from being pulled out from the bladder. This piece will be supported by the strap 70 and its counter-part that will be fixed around the waist and the thigh securely. The bands or straps 63, 64 & 70 may have pieces of their own to be connected to the strap in the belt area in order to make them sturdy and to distribute the weight of the catheter and its related pieces over on the bands that stand around the thigh area. This cradle may also hold the end piece of the tubing that is connected or will be connected to the bag 73. Importantly the connection between these two pieces: the end of the bladder catheter 67 and the tip of the tubing from the bag tip of 69, will be made to allow the tube to be disconnected from the bladder catheter if it was pulled by a patient violently. Importantly, the end of the bladder catheter 67 may be made to close automatically if the tubing for the bag was pulled out. Importantly the tubing that goes to the bag may also have a one way valve marked at 72 that will allow the urine to go into the bag but not to return into the bladder if the level of the tube was placed higher. This is a new security method that the applicant believes is important for times when the bags are accidentally placed above the patient's bladder during transportation, etc and causes the urine from the bag to return into the bladder. The bag for holding the urine is marked at 73. The applicant believes that this model gives the advantage that it will prevent contamination of the catheter by the outer areas from occurring.

FIG. 12. This figure is to show how a cover for a bladder catheter that will consist of two different pieces, one shown at 74–76, is to stand around the penis. It is a piece that will be used only during the placement of this unit and then to be discarded. Then another unit shown at 58–59 (the rest of the body is not shown in this figure ) is to fit the penis and will be kept around it and the bladder catheter in order to prevent contamination. At the time of use the dashed area will allow the placement of the catheter to be done; however, since the catheter will go into the bladder then this part will be squeezed to be flat and then cut and disposed. Then the part shown at 59 will be placed to stand around the catheter and, due to the bands and straps which were shown before and the support unit, will make a stable sturdy unit.

FIG. 13. This figure is very similar to FIG. 1 and is specially chosen to show that the pieces 3 and 5 may have a means of connection like a snap shown at 77 & 78 from piece 5 that will fit matching holes from piece 3 so it will allow these two pieces to be connected to each other easily. This will made a completely closed system that will prevent the catheter passage area from being contaminated. This figure also shows at 79 that this cover may also cover the base of the catheter as well.

FIG. 14. This figure shows the pieces 3 & 5 connected to each other by snaps 77, 78. Also this figure shows how this unit may also have a three-way-stopcock or a valve shown at 80 with its handle marked at 81 in order to allow the bag and related tubing to be disconnected from this catheter when it is needed. This will allow the patient to walk around when the bladder is not full and there is no need for a continuous drainage. These pieces the end of the catheter and the valve may be placed inside a cradle. Also a cradle may be used to connect the end piece of the catheter and the tip of the tubing that goes to the bag.

FIG. 15. This figure shows schematically the make-up of one model of the pieces that are to hold the disinfectant and it is to show how the piece of cotton or the sponge may be held in place securely and also allow it to be functional. This figure shows the vertical cross cut of the body of the space at 82 and the side of this space that is to allow the cover of this unit to stick at 83. Inside this space there are numbers of spears such as 84, 85 and 86 which are made from small spears with a bent tip which this shape will allow easy placement of a cotton ball inside it to occur but not to be able to taken out without force simply due to fact that it will stick to the tip of these pieces. The make-up 8 this unit is also special so that it will not hurt the person's skin since they will not reach it; they also will be made to be somewhat flexible as well.

FIG. 16. This figure is a horizontal cross cut of the same unit shown at previous figure of 15 and at the level of 85–86. This figure is to show schematically the different view of the spores shown in previous figure. In this figure the body of the space is shown at 82 and the spores 84 to 88 are shown and this figure shows how the tip of these spores may be different. The 84 shows the top view of the spore 84 and the 85 shows that this spore 85 also has two sharp side ends as well as one shown in previous FIG. 15. The 86 shows a spore that also has one sharp side spore as well as one that was seen in previous figure 15. The 87 is similar to 86 and the 88 has one sharp end aiming down which can not be seen here.

These units of disinfectants may be made in different sizes and with different medications for different uses so that it will be possible to make them in a series, loosely connected to each other and ready to be used and the inventor believes it will be one simple way of doing this kind of job.

FIG. 17 shows another view of the space that will hold the medication for anesthesia. This figure shows the outer space at 89 and its side at 90 which is for the cover of this unit to stick to it. The body of the medication is marked at 91 and the tip of it is shown at 92. This tip will fit the opening of the external urethra comfortably-for the infusion to occur the sides of this piece with stand around the opening of the urethra in order to prevent the mediation from leaking out. The tip of this unit has a large cover 93 that will allow it to be removed easily. This unit may be connected to the base of the body of its space in order to keep it in its place securely.

FIG. 18 shows a small, soft balloon in shape of a cylinder with an opening in the center may be used to be placed around the catheter between the tip of the penis and the outer end of the catheter in order to prevent the catheter to have a free length and move back and forth. The outer surface of this piece is shown at 94 and its inner opening at 95. This unit may prevent from motion of the catheter back and forth and related transfer of germs inside the bladder. The size and shape of this unit and its consistency and make up may vary.

FIG. 19 shows the cross cut view of the unit shown in previous fig of 18. In this view the outer surface of this unit is shown at 94 and its inner opening at 95. There is an opening in the wall of this unit marked at 97 that will allow this unit to be placed on the catheter and it also shows an adhesive tape 96 that will stick on the surface of both sides of this unit and allows it to be closed and kept in place.

THE DETAILED EXPLANATION OF THIS INVENTION

The need for the insertion of bladder catheters has been recognized for a long time and commonly a person first cleans the outer opening of the urethra of the patient with a disinfectant material such as Iodine, picks up a catheter by sterile gloves, feeds it inside the urethra of the patient and then injects fluid inside the balloon of the catheter. During this process a gel is also opened and applied to the catheter. Also a clean piece of disposable sheet is placed on the area as well. However, handling a catheter which is made from an elastic material and has a tendency to turn, twist and touch the contaminated surrounding is not easy all the time and the fear or chance of infection exists. In these conditions if the patient moves, due to pain or a disturbed mental status then such a chance of contamination is even higher or at least takes a significant effort to prevent. Prevention of contamination has been a priority in medicine and now in the age of AIDS it is even more important. The cleaner the procedure is, the better it will be. Also the time used for a procedure is important as well when the need for medical help is expensive and rising. Therefore if a procedure could cut the time and chance of contamination it would be a superior product and a better unit to be chosen. Also if the size of unit is smaller it will be better as well since it has the advantage over the bigger and bulkier units.

Importantly, the unit that has everything ready to use in one unit is better than a unit in which the person has to prepare different parts for use. For these reasons this inventor introduces a unit that has many advantages: first, it will eliminate or significantly decrease the chance of contamination. This will be done with the use of a catheter which has a protective cover on it which will protect it from the contaminated surroundings and it will allow the catheter to be fed to a patient by moving the catheter inside this cover. This cover will be made from any proper polymer; it may be made from a clear material to allow better visualization to occur. In this method the catheter is caged inside this tubular cover which is soft, protective and flexible and has one front end that may be large and properly shaped to go over the tip of the male penis or to stand around the opening of the urethra of the female patient. There will also be a rear end that will go over the end piece of the bladder catheter or to hold that part inside it securely. In the male the tip of this unit will go over the penis and in the female it will be held securely around the opening of the urethra so that this shaping will allow the unit to be held in place easily and securely. After the cleaning job is done and the catheter is in proper position then the catheter can be gently pushed forward by holding it thorough the body of the cover and entering it into the opening of the urethra. Importantly the patient will receive an injection of anesthetizing gel from a disposable unit so that the procedure can be done without pain and discomfort.

Such a cover may be made to have a series of improvements in order to facilitate such a job. For example:

A. The unit may use a special grip such as one shown at no 49 FIG. 7 or patches of hard or semi-hard polymer such as one shown at 65 FIG. 11 that will allow the cover to be squeezed against the wall of the catheter in order to allow an easier and stronger grip of the catheter to occur. There may be more than one piece 49 which may be moved from one spot to another.

B. These catheter covers may be made to have extra spots, bumps or lines of materials (same as the wall of the cover or different kind) on their outer surface in order to allow a better grip of this unit and the catheter to occur. The inner surface of these covers may also have these kinds of changes as well.

C. The outer surface of these catheter covers may have a series of tabs such as the ones shown at 54 FIG. 8 to allow the body of the cover to be held and moved easily. These will be made from the same material as the wall of the cover or other kinds.

D. These catheter covers may be made to have specially shaped walls such as the one shown at 50 & 51 FIG. 7 that are to allow the catheter to be pushed forward easily but not to allow it to slide and come back when the pushing is stopped. This wall may be placed in any proper area and several can be used.

E. The end piece of some models of these protective bladder catheter covers may be made to have an opening no 55 FIG. 9 that allows injection of a gel or a medicated material such as an anesthetic material inside the cover to occur. This will decrease the chance of contamination of these units.

F. Some other models of these covers may be made to have a tube of gel or medicated material such as the one shown at 56 FIG. 10 in place and connected to the wall of the cover. This unit has a wall 57 that at the time of use will be broken or torn by tilting, twisting or a similar simple mechanism so it will allow the injection of the gel or a medicated material inside the cover to occur easily. This is to facilitate the job of the application of gel or medications further and to eliminate the job of application of gel over the catheter manually.

G. Importantly, these units can also give better protection to the units by having a series of bands connected to the various parts of these covers, from the base of the covers to the person's body. The end pieces and the cradle areas may also have bands and straps to be wrapped around the body in the belt area or the thigh or to be connected to these areas by use of adhesives and similar methods. Overall, they are to provide a very effective means of holding this piece in place.

H. This unit will also allow the disconnection of one piece of tubing: the bladder catheter or the tubing which is disconnected if a confused or irritated patient attempted to take it off. This will prevent a catheter (with an inflated balloon in its tip) being pulled out and ripping the urethra. This is a very important issue and was previously pointed out in the applicant's U.S. Pat. No. 5,406,606. In these models, various means to allow such a disconnection will be used. Even an alarm system may be connected to inform the nursing staff of the occurrence.

I. This application also introduces the use of a valve or a three-way stopcock to be connected to the end of these catheters to allow the similar goal mentioned in the U.S. Pat. No. 5,460,606 to be achieved. That is to allow the urine flow to be interrupted when it is not needed to occur. This will allow the patient to walk around without having a bag connected to it. Also, to open the valve for emptying the bladder.

J. Various types of pieces or cradles may also be connected to the end of this unit in order to allow the end of these bladder catheters to be modified and controlled. These may be shaped like a suit case with a body to hold the catheter parts and their connections, and a cover that will go over these parts to keep them inside securely. These cradles may have a valve as part of their construction to connect the catheter and the tubing from the bag. They may have a design to allow the connection of the tip of the tubing from the bag to be done in a desired way. This will allow the tubing from the bag to disconnect from the catheter when pulled by a confused patient.

These cradles may have different shapes, sizes and designs. They may be made from soft or rigid polymers and will keep the other parts inside them or around their bodies, and importantly will allow easy connection of the bands and straps to their sides as well.

These pieces may do different jobs: connections, safety, simplification of the connections, acting as a valve, etc.

H. In some models the catheter cover may also allow special medication to be kept inside it in form of a gel, powder or even liquid for different proposes, such as prevention from infection. This method will expose the catheter to these medications and materials. The external urethra may be also medicated by this method.

Also, in order to facilitate the process of cleaning, this unit will have a cover piece similar to the one shown in FIG. 4 & 6 which allows an easy, less time consuming cleaning and anesthetic application of the external urethra to occur. In this method a large protective cover made from a layer of polymer such as thin vinyl combined with some other materials such as paper will be used to prevent transpassing liquid and gems. This piece 18 also has a tubing 19 that will stand around the penis. This tubing may be made to be elastic or to have an accordion type wall as well. The tube 19 due to its elastic or accordion type wall will allow its length to be adjusted according to the length of the penis so that the tip of the penis or the external urethra in ladies will be properly positioned in the tip of this opening. When this piece is in place then the opening of the urethra can be cleaned easily without being contaminated or contaminating the hands of the user. This cover will have a series of sponges or cotton balls of disinfectant that are to allow rapid and effective cleaning. One model of these is shown as a series of spaces A, B & C that are like pockets made from a layer of polymer such as commonly used vinyl, and each one of these spaces (such as the one shown at 24) will hold a piece of disinfectant such as sponge or cotton balls 25 saturated with iodine or other disinfectants so that it can be used for cleaning the area easily. The opening of this cover will have a protective cover 26 to be removed before use. The tabs 27 and 28 are designed to allow an easy and quick separation of these covers. These units will be placed conveniently or connected to each other by small bands that will allow them to be located easily and will prevent them from falling and therefore will be handled easily.

This unit also will have a pocket such as the one shown at 29 that will hold a container of anesthetic gel such as no 30 inside it. The container of this anesthetic gel 30 may have different shapes or makeups such as being made similar to a tubing of tooth paste or in the shape of a rubber bulb or a similar polymer with a properly sized (the length of about 1 to 2 cm and the diameter of about 6 to 8 mm and a curved tip) rigid or semi rigid end tip which will fit the orifice of the external urethra easily. The base of this tip will be made almost flat to prevent trauma due to over insertion of the tip.

At the time of use the tip of this unit 32 will be inserted into the external urethra to allow injection of the anesthetic medication inside the urethra to occur easily in order to prevent pain and irritation. The tip 32 of this unit will be made to have a cover 31 with a large handle so that it can be opened and removed easily.

This unit may also have a small envelope or bag 41 FIG. 6 to allow the used material of these units to be placed inside it for a rapid and comfortable disposal. This pocket is to have a flap or rim to keep the used materials inside.

This unit also will have a line 38 FIG. 6 to allow this unit to be torn off and removed easily after use. These units are also to have a series of lines, markings, writings and figures that will allow special directions or instructions to be communicated to the users.

The tubing that will go around the penis may have special indentations outside its surface in order to make the job of holding it and the grip easier, it may also have such bumps inside to allow it to be held easily.

Importantly different parts, pieces and areas of these units may have different sizes and designs; for example the pieces 4, 5 and 6 FIG. 1 from the cover may have different sizes. The size of piece 5 may be smaller or larger, the piece 4 may be longer or shorter, it may have different diameters. Its wall may have different constructions, bumps on its surfaces, elasticity, etc. The same is also true about the different parts and pieces of the other parts as well. This is to allow different units to be made for different sized and shaped patients and also to satisfy the needs of different users.

Importantly these units also will have a handy unit of water similar to a bulb or a syringe in order to allow a rapid infusion of water inside the balloon of the catheter. The person is to squeeze the bulb or syringe that contains water or air into the balloon in order to secure the placement of the catheter. Then he/she can remove the cover by cutting it along the lines made for this purpose and to remove it.

Also importantly the bladder catheter or the tubing that carries the urine to a bag may have a one-way valve no 72 FIG. 11 so that it will allow the urine to go toward the bag but not back to the bladder. This is a safety measure to prevent urine returning back to the bladder at times when the patient is sitting in the chair and the bag is hanging on the side of the bed or when the patient is being transferred.

Importantly, some models of the bladder catheter may be made to have the syringe for the injection of the fluid to the balloon of the tip of the catheter to be already connected and in place to be used. This is to decrease the amount of time and the effort needed for this job to be done, since it would need to have a discontinuation of the process to be done and both hands to be used for this purpose.

Importantly the tip of this container may be connected to the base of its cover so that this technique plus a larger cap-handle will allow it to be removed easily and with lesser effort.

Importantly, this unit will be modified so that the units for the ladies are to be shaped to fit their external genitalia comfortably. The piece will have a mild curve and as well as providing the opening in a proper place. These units may also have a smaller tube-shaped piece similar to no 19 FIG. 4 since naturally it is not needed as much. The piece 20 will be still useful to cover the hand of the user and prevent contact between the user's hand and the urethra area and prevent contamination. However, in some models this piece may be eliminated. The size, shape, curvature and the other characteristics of this unit may vary.

Importantly it should be mentioned that every type of bladder catheter may be utilized. Naturally it will be necessary to modify each model with a particular catheter to match its length and shape. This will also be true with the use of specially designed catheters referred to U.S. Pat. No. 5,460,606.

Importantly, these covers may be made ready for use, and to allow the catheters to be inserted inside it prior to use or packaging, so that the catheters that do not have such a cover may also be covered by these units.

Importantly, the outer cover of this tubing may have patches of semi-hard or hard polymer that will allow the unit to be squeezed by holding these two patches simultaneously. These patches may be placed on this cover intermittently.

The body of this cover for catheter (which is like a tubing) may be made from any proper thickness, size and shape. It can be made from a clear thin, flat, vinyl or the tubing may be made from a somewhat thicker polymer with a predetermined shape such as a cut which is round, rectangular, flat, etc. Although all are to be made squeeze-able. The body of this cover may have a consistency, a skeleton of its own, a circular spring, a series of springs or differently-shaped springs inside it or on its wall in order to hold the cover somewhat away and separate from the bladder catheter (to allow it to be moved inside easily). Importantly this cover may be connected to a series of bands or straps of the same size or of different shapes, sizes and materials in order to allow the cover to be held in place securely. These bands are to go around the belt and the thigh area, etc. Also, importantly adhesive films and materials may be used for this purpose. The tubing or its straps may have a band of adhesive substance covered by a protective layer that will allow them to be stuck to the skin and to allow better stability when needed. These bands or straps may be connected to any areas of this unit; it may be in the tip of the unit, the body or in the base of the unit as needed. These bands or straps may also be removably connected to such a unit; it can be connected to the unit on a desired and optional basis to be removed later. These bands and straps are to go around the belt and thigh areas. Importantly the connection of the bladder tubing to the tubing from the bag may be made separable so it can be disconnected if the tubing to the bag was pulled out. An alarm may also be connected to this connection point so it will go off if the patient removed the catheter or attempted to do so. The shape, size, coloring, thickness, relative sizes of the pieces and the other important characteristics of this unit may vary from unit to unit.

Naturally these modifications will also apply to the units for the ladies and these units will be shaped to fit the body of the penis of the men or the surrounding area of the female's external urethra comfortably so that it will allow an easy placement. Also, the base of these units will be made to have bands, straps or similar means connected to it so it will allow the unit to be positioned and kept in the area securely and not to allow the user to be able to bring his or her hand to the catheter and pull it out.

These cover units may also have some other safety measures as well. The end piece of this cover unit may also have a piece similar to the one shown at 66 that will function as a cradle to hold the end of the catheter inside itself safely and to prevent it from being pulled out. This piece will be made from a polymer and may be made from a rigid or a semi-rigid material supported and held in place by a series of straps such as the one shown at 70 and its counterpart from the other side so that it will be kept by these straps that go around the waist and the thigh. This cradle may also have a valve to allow this catheter to be opened or closed easily. This cradle may function as the connection piece between the bladder catheter and the tubing from the bag so that it will allow these two pieces to be connected to each other safely.

This piece will be designed to allow the tubing from the bag to be pulled away without the bladder catheter being pulled out. This will prevent patients from pulling the bladder catheter out and causing damage to their urethras. In such a model, the end of the bladder catheter may be made to close automatically if the tubing for the bag was pulled out. This can be done by many simple techniques, for example a spring could go over the end piece of the bladder tubing so that when the inner tubing of the bag is pulled out the spring would cause the closure of this piece to occur.

In these units the syringe of water may be connected to the tip of the opening for inflation of the balloon and to be ready to be used so that there will be no need to connect it later. A piece of plastic will be placed around the plunger to prevent it from being pushed accidentally; the user has to remove this piece to inject the water inside the balloon.

Also importantly, the piece that is designed for cleaning the area such as the one shown at no 5-4-6 FIG. 1 may have a couple of snaps as shown at 77 & 78 FIG. 13 on the surface of the piece 5 that will allow matching pieces from the piece 3 from the bladder catheter cover to be connected to each other. The advantage of this system will be that it will totally eliminate the hand of the user from touching the clean area, and causing contamination. At the time of use (after this connection is made), as shown in FIG. 14, the piece 3 and the cover 2 can be pushed forward (toward the body of the person) to cause the piece 4 to collapse and allow the piece 2 to go over the penis and to make a completely covered clean area for this procedure.

Also, in order to prevent the bladder catheter from moving back and forth and carrying germs inside, a small, soft balloon in the shape of a cylinder with an opening in the center may be used to be placed around the catheter between the tip of the penis and the outer end of the catheter. This piece will have an opening in its wall (no 97 FIG. 19) in order to allow this unit to be placed on the catheter. The unit will be closed by an adhesive tape that will stick on the surface of both sides of this unit. The size, thickness, hardness and the other characteristics of this unit may vary from unit to unit and it will have different sizes to be chosen from for each particular patient.

It is to be considered that importantly every type of bag that can be used for the collection of urine may also be used with these units. These bags can be plastic bags, bags with small spaces or units that allow the volume of the hourly urine to be known, etc.

Methods of use:

At the time of use the patient will be placed in supine position, then the base cover 6 or 18 will be spread over him/her properly so that the penis or the external opening of the urethra will be placed in the opening no 21 FIG. 4. The smaller cover 20 will be around the opening of the urethra. Then the user will open the cleaning sponges located at A, B and C so that it will clean the area easily. As was mentioned in FIG. 4 these sponges or cotton balls may have connective means or a system to hold them in place at the time of use so that they would not need to be taken out and also to be disposed. The applicant believes that this is a very simple, easy and yet important and economical means that may be used in many other occasions as well. These can be made separate and in a series to be cut in the numbers (two, three or four of them etc.) needed and used for cleaning any place. After the cleaning of the outer urethra is over then the user will use the anesthetic material by injecting it into the urethra of the patient. This is more important in the men than women. In the ladies the mere use of the gel may be enough to prevent the hurting during this insertion. Importantly the tip of the container of the anesthetic material may be connected to the cover so that it can be removed when the cover is removed; another option is having a larger cap handle which will allow the cap to be removed easily and with lesser effort. After this step is over the user will inject the lubrication gel into the body of the cover at area 33 FIG. 3 or will use the units shown at FIG. 9 & 10 and then proceed to push the bladder catheter forward and gently to place it inside the urethra. This will be continued until the catheter is in the right place; then the user will inject water inside the balloon of the bladder catheter and connect it properly to the tubing from the bag or container. Then the user can tear off the cover and remove the whole unit. This unit then can be wrapped and may also have a piece of adhesive tape on its rear surface to allow it to be safely closed for disposal.

Importantly, the applicant would like to mention that such a covering unit may be modified to be used with units such as an Intra-Aortic balloon pump and similar catheters as well. Also importantly the method and pieces that are mentioned for cleaning the area shown at A, B & C FIG. 4 & 6 may also be made in a series connected by a small plastic band to allow them to be used for the cleaning of many skin wounds and similar things. These can be made to be a simple, easy and economical means for these purposes.

This invention gives many options for the users. A simple model of this unit may be used at the time of insertion of the catheter and to be removed after use, a system that will make total closure of the system and avoid contamination and a system that has protective measures and allows the catheter to be kept in place securely regardless of its weight. The means of allowing the catheter to be pulled without disturbing the whole system is also mentioned. These cover units may be made alone so that they can be added to the catheters at the time of use. They will be made in different sizes and shapes to fit different catheters as well. The pieces that go over the penis will be made larger to fit that part of the body easily and its material may be chosen to be different as well.

The applicant also would like to mention that importantly the teaching and models shown in this application can be modified to make many useful and different models as well. These units may be made in a simple tubing form that will cover the catheter and its related pieces and it can be made to be more complicated with the pieces that will allow the catheter to be held in place securely and to have the mechanism that prevents the catheter from being pulled out of the bladder.

Importantly the size, shape, coloring, thickness, relative sizes of the pieces and the other important characteristics of these units and its components may vary from unit to unit.

I claim:

1. A clean urinary catheter insertion system comprising:
   a first tubular part for external placement over the external urethra, said first tubular part having a distal end for placement toward the area surrounding the urethra and a proximal end opposite said distal end adapted for connection to a distal end of a second tubular part;

a second tubular part separate from said first tubular part and comprising a distal end adapted for connection to said proximal end of said first tubular part and a proximal end;

a urinary catheter disposed within said second tubular part; and connection means for connecting the distal end of said second tubular part to the proximal end of said first tubular part.

2. A clean urinary catheter insertion system as set forth in claim 1 in which said first tubular part comprises an apron at its distal end for covering the area surrounding the external urethra.

3. A clean urinary catheter insertion system as set forth in claim 1 further including an attachment means for securing said first and second tubular parts to a person, said catheter comprises a proximal end, and said system further includes a tubular section having a distal end separably connected to said proximal end of said catheter by a separable connection that disconnects said tubular section from said catheter when a certain pulling force is applied to said tubular section, said second tubular part covering said separable connection while said tubular section extends out of a proximal end of said second tubular part.

4. A clean urinary catheter insertion system as set forth in claim 1 including attachment means for attaching said first and second tubular parts to a person.

5. A clean urinary catheter insertion system as set forth in claim 1 in which said first tubular part comprises means providing for its length to be adjusted.

6. A clean urinary catheter insertion system as set forth in claim 1 in which the exterior of at least one of said first and second tubular parts comprises surface features providing other than a smooth circumferential wall in order to facilitate manual gripping.

7. A clean urinary catheter insertion system as set forth in claim 1 in which said second tubular part comprises an internal funnel near the distal end thereof and through which said catheter passes when said catheter is advanced distally of said second tubular part to enter said first tubular part.

8. A clean urinary catheter insertion system as set forth in claim 7 in which said funnel is operatively associated with said catheter to prevent any appreciable withdrawal of said catheter proximal to said second tubular part after said catheter has been distally advanced to pass through said funnel.

9. A clean urinary catheter insertion system as set forth in claim 7 in which a lubrication- or medication-containing dispenser is disposed within said second tubular part to dispense lubrication and/or medication onto the catheter as it passes through said funnel.

10. A clean urinary catheter insertion system as set forth in claim 1 in which a flap of material is externally mounted on said first tubular part and contains treatment means for treating the external urethra prior to catheter insertion.

11. A clean urinary catheter insertion system as set forth in claim 10 in which said flap contains various forms of said treatment means in various treatment holders on said flap.

12. A clean urinary catheter insertion system as set forth in claim 11 in which said various treatment holders comprise means for allowing treatment means to be applied without removal from the holders.

13. A part for a clean urinary catheter insertion system comprising a urinary catheter, said part comprising:

a tubular part for external placement over the external urethra prior insertion of such a urinary catheter into urethral opening, said tubular part having, prior to its placement over the external urethra, an apron surrounding distal end opening thereof for placement over the area surrounding the external urethra and a proximal end opening opposite said distal end opening, and a shield extending radially outwardly of said proximal end opening, said tubular part having a length providing for t urethral opening to protrude through said proximal end opening when placed over the external urethra.

14. A part for a clean urinary catheter insertion system as set forth in claim 13 in which said tubular part comprises means providing for its length to b adjusted so that the urethral opening can protrude through said proximal end opening when said tubular part is placed over the external urethra, and further including, in combination with said tubular part, a further tubular part having a distal end having an opening and joined to the proximal end of said first-mentioned tubular part to place said tubular parts' openings in alignment.

15. A part and further part for a clean urinary catheter insertion system as set forth in claim 14 in which said further tubular part has an internal annular wall disposed within a distal end portion of said further tubular part to locate the tip end of a penis within said further tubular part when the length of said first tubular part is contracted to allow the tip of the penis to enter the further tubular part.

16. A part and further part for a clean urinary catheter insertion system as set forth in claim 15 in which a lubrication- or medication-containing dispenser is disposed within said further tubular part proximate said internal annular wall.

17. A clean urinary catheter insertion system for a urinary catheter comprising:

tubular structure, comprising a proximal end opening and a distal end opening, for external placement over the external urethra prior to insertion of such a urinary catheter into a urethral opening to provide for the urethra opening to protrude through said proximal end opening when placed over the external urethra prior to insertion of such a urinary catheter into a urethral opening;

a flap of material externally mounted on said tubular structure;

and treatment means disposed on said flap at a location that is spaced radially outwardly away from said tubular structure for treating the external urethra prior to catheter insertion while said treatment means remains on said flap.

18. A clean urinary catheter insertion system as set forth in claim 17 in which said flap contains various forms of said treatment means in various treatment holders on said flap.

19. A clean urinary catheter insertion system as set forth in claim 18 in which said various treatment holders comprise means for allowing various treatment means to be applied without removal from the holders.

20. A clean urinary catheter insertion system as set forth in claim 18 in which said various treatment means comprises lubricant, antiseptic, soft wiping material, a catheter, and a waste receptacle.

* * * * *